United States Patent
Holmström

(10) Patent No.: US 7,389,142 B2
(45) Date of Patent: Jun. 17, 2008

(54) HEART MONITORING DEVICE, SYSTEM AND METHOD

(75) Inventor: Nils Holmström, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 872 days.

(21) Appl. No.: 10/630,468

(22) Filed: Jul. 30, 2003

(65) Prior Publication Data

US 2004/0082974 A1    Apr. 29, 2004

(30) Foreign Application Priority Data

Jul. 30, 2002    (SE)    .................... 0202347

(51) Int. Cl.
*A61N 1/00*    (2006.01)
(52) U.S. Cl. ...................................... 607/18
(58) Field of Classification Search ............ 607/22, 607/18, 17; 600/513, 364
See application file for complete search history.

(56) References Cited

U.S. PATENT DOCUMENTS

| | | | |
|---|---|---|---|
| 4,202,339 A * | 5/1980 | Wirtzfeld et al. ............ 607/22 |
| 4,453,537 A | 6/1984 | Spitzer | |
| 5,156,147 A * | 10/1992 | Warren et al. .............. 607/24 |
| 5,176,137 A * | 1/1993 | Erickson et al. ............ 607/4 |
| 5,199,428 A * | 4/1993 | Obel et al. ................. 607/44 |
| 5,213,098 A | 5/1993 | Bennett et al. | |
| 5,342,406 A * | 8/1994 | Thompson .................. 607/22 |
| 5,582,170 A | 12/1996 | Soller | |
| 5,720,768 A | 2/1998 | Verboven-Nelissen | |
| 5,741,211 A * | 4/1998 | Renirie et al. ............. 600/300 |
| 6,070,100 A | 5/2000 | Bakels et al. | |
| 6,236,873 B1 | 5/2001 | Holmström | |
| 6,752,765 B1 * | 6/2004 | Jensen et al. ............. 600/536 |
| 2002/0107553 A1 * | 8/2002 | Hill et al. .................. 607/18 |

FOREIGN PATENT DOCUMENTS

| | | |
|---|---|---|
| EP | 0 467 213 | 7/1991 |
| EP | 0 504 935 | 9/1992 |
| WO | WO 02/053026 | 7/2002 |

* cited by examiner

*Primary Examiner*—Carl Layno
*Assistant Examiner*—Jon-Eric Morales
(74) *Attorney, Agent, or Firm*—Schiff Hardin LLP

(57) ABSTRACT

In an implantable heart-monitoring device and system, and a heart-monitoring method, a control circuit is connected to one or more sensors, a first of which is positionable in the coronary sinus region of a heart and senses at least one blood constituent, and at least one other of the sensors supplying a signal to the control circuit indicative of the activity of the heart. In response to signals from the first sensor and with information about the activity of the heart from the other sensor, the control circuit determines a first value of the blood constituent during a first portion of a heart cycle, and determines a second value of the blood constituent during a second portion of the heart cycle.

33 Claims, 4 Drawing Sheets

HEART MONITORING DEVICE, SYSTEM AND METHOD

BACKGROUND OF THE INVENTION

1. Field of the Invention

The present invention relates to an implantable heart monitoring device of the type having a control circuit connected to one or more sensors suited to be positioned in or at the heart of a living being, at least a first of the sensors being positionable in the coronary sinus region of the heart and arranged to sense at least one constituent of blood, and wherein the control circuit receives signals from the first sensor, which are related to the blood constituent, and wherein the control circuit senses the activity of the heart, via signals from one or more of the sensors, such that events signifying a heart cycle are detectable by the control circuit. The invention also relates to a heart monitoring system including such a heart monitoring device and a method for monitoring a heart.

2. Description of the Prior Art

Many different devices for monitoring the performance of a heart are known. Often these devices are also able to deliver stimulation pulses to the heart. The devices are often able to sense the electrical activity in the heart. It is also known to sense other physiological parameters, such as pressure, oxygen level, pH, nitric oxide, carbon dioxide, etc.

U.S. Pat. No. 5,213,098 discloses a cardiac stimulator with an oxygen saturation sensor positioned in the coronary sinus of the heart. The device is also able to sense the blood pressure and the electrical activity of the heart. The stimulator may be used to control the atrial stimulation in order to improve the filling of the ventricles.

U.S. Pat. No. 5,199,428 discloses a device for detecting myocardial ischemia. A pH sensor or an oxygen saturation sensor may be positioned in the coronary sinus. The device can be used to stimulate for example the left and/or right carotid sinus nerves in order to decrease cardiac workload.

U.S. Pat. No. 6,236,873 discloses an electrochemical sensor for measuring the oxygen content in blood.

U.S. Pat. No. 4,202,339 describes a sensor for measuring the oxygen saturation level in blood.

U.S. Pat. No. 4,453,537 discloses a device for sensing, inter alia, the carbon dioxide content in the blood.

U.S. Pat. No. 5,582,170 discloses a fiber optic sensor for sensing the nitric oxide content in blood.

U.S. Pat. No. 5,720,768 discloses different possible electrode positions in order to stimulate or sense the different chambers of the heart.

U.S. Pat. No. 6,070,100 discloses that electrodes may be positioned in both the left and the right atrium as well as in or at the left and the right ventricles. The document describes the possibility of sensing the impedance between different electrodes. The sensed impedance values may be used to improve the cardiac output.

U.S. Pat. No. 5,156,147 discloses a pacemaker which has a hemodynamic sensor which is arranged to provide a signal representing the pumping performance of the heart. The hemodynamic sensor may be a piezoelectric pressure sensor.

SUMMARY OF THE INVENTION

An object of the present invention is to provide an implantable heart-monitoring device, which in a relatively simple manner is able to monitor the condition of a heart. A further object is to provide such a device, which by means of a single sensor for a blood constituent, is able to derive information about the heart condition. A still further object is to provide an implantable heart monitoring system including such a device and a method for monitoring the condition of a heart.

The above object concerning the device are achieved in accordance with the invention in an implantable heart monitoring device of the type initially described wherein the control circuit, in response to signals from a first sensor, determines a first value related to the blood constituent during a first portion of a heart cycle, and in response to signals from the first sensor, determines a second value related to the blood constituent during a second portion of the heart cycle.

With the heart-monitoring device according to the invention, it is thus possible to obtain, from the same sensor, different values for a blood constituent during different portions of a heart cycle. These values, and the relationship between these values, can provide important information about the condition of the heart. In particular, if the first sensor is positioned in the coronary sinus of the heart, important information may be obtained. The blood in the coronary sinus is primarily the blood which comes from the cardiac venous system and exits into the right atrium. However, some blood may also enter from the right atrium into the coronary sinus. The blood in the right atrium normally represents the mixed venous blood of the body. By monitoring the blood constituent during different portions of a heart cycle, important information of the condition of the heart may be obtained, since these monitored blood constituent values may represent both cardiac venous blood and mixed venous blood. The blood constituent that is sensed by the first sensor primarily will be exemplified by the oxygen content in the blood, in particular by the partial pressure of oxygen in the blood. However, the invention is also applicable for sensing other blood constituents, such as the saturation level of oxygen, the carbon dioxide content, the content of nitric oxide, the pH-level of the blood or the temperature etc. Since the heart monitoring device also senses the activity of the heart, the control circuit also can measure the blood constituent during different well defined portions of the heart cycle.

According to one preferred embodiment of the invention, the control circuit operates such that the first portion of the heart cycle is during the diastolic portion of the heart cycle and the second portion of the heart cycle is during the systolic portion of the heart cycle. In particular, the second portion of the heart cycle can be within the later 70% of the systolic portion of the heart cycle. By selecting the first and second portions of the heart cycle in this manner, important information about the difference of the blood constituent in, for example, cardiac venous blood and mixed venous blood can be obtained.

In an embodiment of the invention, the blood constituent in question is oxygen as has been explained above. The oxygen concentration in the cardiac venous blood and in the mixed venous blood carries important information about the heart condition.

In an embodiment of the invention, the control circuit monitors the first and second values over a number of heart cycles, it is thereby possible to monitor how the first and second values change with time.

In another embodiment of the invention, the control circuit triggers the heart-monitoring device to carry out at least one measure if the first and second values and/or a relationship between the first and second values fulfill a predefined condition. The condition may be, for example, that the first value is lower than a first predefined level and the second value is higher than a second predefined level. The condition alternatively may be that the first value has decreased more than a first predefined amount over a number of heart cycles while the second value has decreased less than a second predefined amount over the same heart cycles. The relationship between said first and second values and/or how these values change with time carry important information about the heart condition. The measure to be carried out may be, for example, to control the delivery of stimulation pulses to the heart. Another measure can be to deliver a drug in response to the monitored values. A still further measure can be to deliver a warning signal. These measures thus may be used to improve the heart condition or to warn a patient or a physician to pressure, for example, a suitable drug to be taken by the patient.

In another embodiment of the invention, the device enables the sensing of the physical activity level of a living being in whom the heart-monitoring device is implanted, and the control circuit takes the sensed activity into account when determining whether the aforementioned measure should be carried out. The monitored values of the blood constituent may be analyzed in relation to the activity level of the living being in question. This enables an improved basis for decisions concerning a possible measure to be carried out.

The above object also is achieved in a heart monitoring system having a heart monitoring device according to any of the above embodiments and one or more leads connected to the heart monitoring device, wherein the one or more sensors, including the first sensor is/are positioned on the leads. The invention thus provides a system which may be implanted into a living being.

In a preferred embodiment of the system, the first sensor and said control circuit are arranged to sense the amount of oxygen in the blood. Preferably, the first sensor is located on a first lead, which is suited to be introduced into the coronary sinus of the heart such that the first sensor can be positioned in the coronary sinus. Thus, the above-mentioned advantages of positioning a sensor in the coronary sinus are obtained.

In a further embodiment of the system, the first lead has at least a second sensor or electrode, this second sensor or electrode member being closer to the distal end of the first lead than said first sensor, and the first lead is designed such that said second sensor or electrode can be introduced via the coronary sinus into a cardiac vein. Advantageously, the control circuit is arranged to enable the delivery of stimulation pulses to said second sensor or electrode member. Such a sensor or electrode member may be positioned via the great cardiac vein into for example the posterior, lateral or anterior vein of the left ventricle and may be used to stimulate the left ventricle of the heart.

In a further embodiment, the system has, in addition to the first lead, at least a second lead, this second lead having at least a third sensor or electrode member suited to be positioned in the right ventricle of the heart. Preferably, the control circuit delivers stimulation pulses to both the second sensor or electrode and to the third sensor or electrode, so as to enable the delivery of stimulating pulses to both ventricles of the heart. The third sensor or electrode, of course, also may be used to sense events in the heart. Stimulating both ventricles of the is advantageous, for example, when treating patients suffering from congestive heart failure.

As stated above, the invention also concerns a method for heart monitoring, using this system described above. In this method, the system is implanted into a living being, with said first sensor positioned in the coronary sinus region in the heart of the living being and wherein at least the first and second values of the blood constituent are determined as initially described in connection with the inventive device. The above-mentioned advantage is thereby obtained.

The first and second portions of the heart cycle may be chosen such that the first value is related to the blood constituent in blood from the cardiac venous system and such that the second value is related to the blood constituent in mixed venous blood. The method, for example, may be used to detect a state of ischemia in the heart. As explained above in connection with the system, the method may be used to sense the blood constituent oxygen. The method thus may be used to deliver a warning signal or to carry out a therapy if the first and second values and/or a relationship between the first and second values fulfill a predefined condition.

DESCRIPTION OF THE PREFERRED EMBODIMENTS

Figure 1:
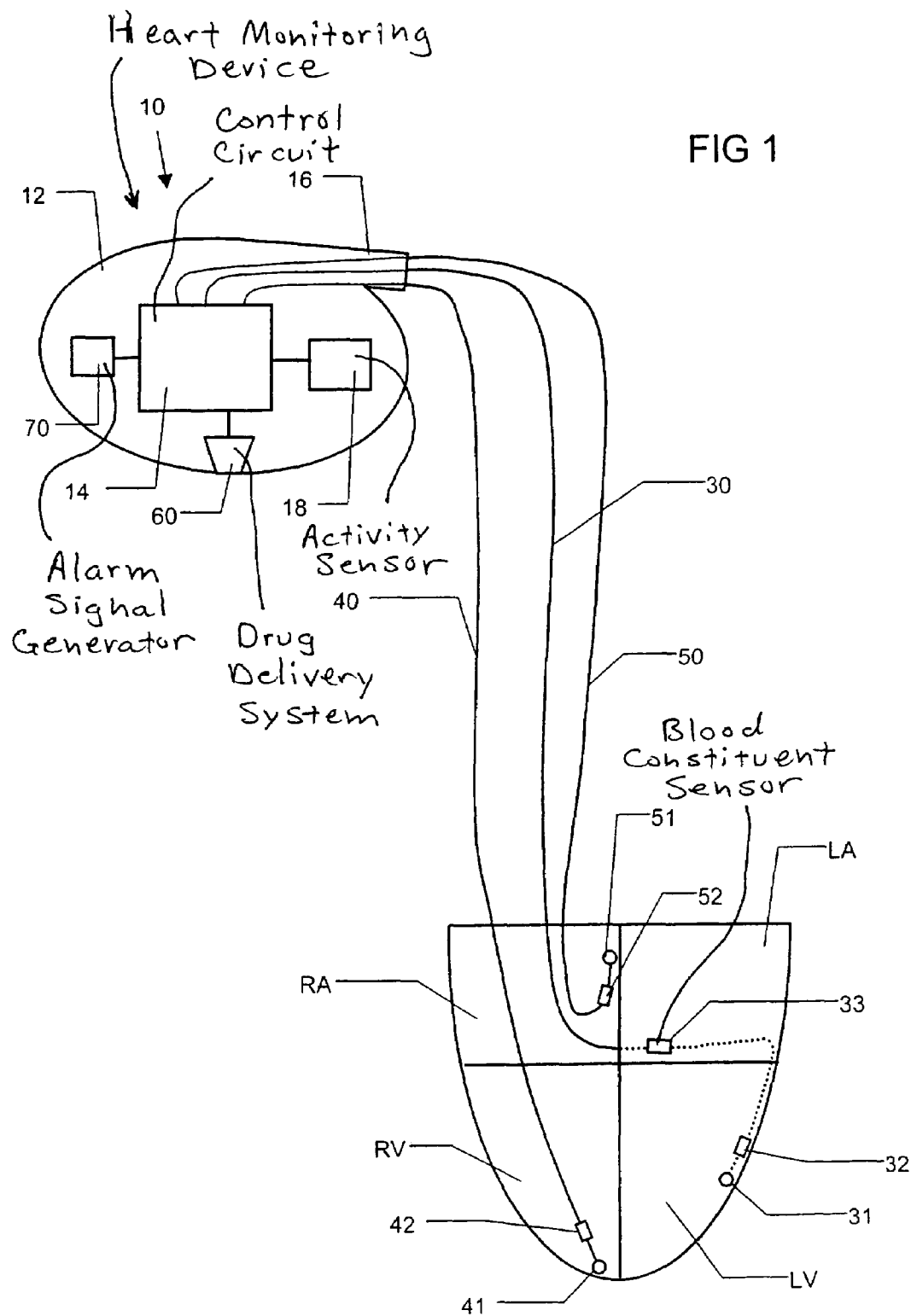
FIG. 1 shows schematically a heart monitoring system with a heart-monitoring device connected to leads with sensor or electrode positioned in a heart, in accordance with the invention.

An embodiment of the invention will first be described with reference to FIG. 1. FIG. 1 shows schematically a heart-monitoring device 10. The device 10 has a housing 12. The device 10 is implantable in a human or animal. A control circuit 14 is arranged within the housing 12. The device 10 may include an activity sensor 18 in order to enable sensing of the activity level of the living being into which the heart-monitoring device 10 is implanted. The device 10 has a connector portion 16 to which one or more leads 30, 40, 50 may be connected. In the shown embodiment, there are three leads 30, 40, 50, however, the number of leads may be more or less than three.

A first lead 30 carries a first sensor 33, which is adapted to be positioned in the coronary sinus region of the heart. The first sensor 33 senses at least one constituent of blood. The first lead 30 may also carry a second sensor or electrode 31, 32 located closer to the distal end of the first lead 30 than the first sensor member 33. The illustrated embodiment also shows a second lead 40 with at least a third sensor or electrode 41, 42. Furthermore, a third lead 50 is shown with sensor or electrode 51, 52. The sensors or electrodes 31, 41, 51 are located at the tip portion of the respective lead 30, 40, and 50. These members therefore may be called tip electrodes. The electrodes 32, 42, 52 are located a little further up along the respective leads 30, 40, 50 and may be called ring electrodes. These sensors or electrodes 31, 32, 41, 42, 51, 52 are thus arranged as bipolar electrodes. It is of course possible that instead unipolar electrodes are used. The electrodes 31, 32, 41, 42, 51, 52 may be used to sense the activity of the heart and/or to deliver stimulation pulses to the heart.

At least one sensor, in the embodiment of FIG. 1, the sensor 33 is designed to sense a blood constituent. The blood constituent, for example, may be the partial pressure of oxygen in the blood. As mentioned above, however, the sensor 33 instead may sense other blood constituents, such as the oxygen saturation level, carbon dioxide, nitric oxide, pH or temperature.

FIG. 1 also schematically shows a heart with a right atrium RA, a right ventricle RV, a left atrium LA and a left ventricle LV. The first lead 30 with the first sensor 33 is designed such that it can be introduced via the right atrium RA into the coronary sinus region of the heart. The first lead 30 also may be introduced further into the coronary venous system such that the second sensor or electrode 31, 32 is introduced, for example via the great cardiac vein, into the posterior, lateral or anterior vein of the left ventricle. With such a position of the second sensor or electrode 31, 32, it is possible to stimulate the left ventricle LV of the heart. The portion of the first lead 30 that is introduced into the cardiac venous system is here shown with a hatched line.

The second lead 40 is here shown to be introduced via the right atrium RA into the right ventricle RV such that the third sensor or electrode 41, 42 is located close to the apex of the right ventricle RV. The third sensor or electrode 41, 42 may be used to sense the electrical activity of the heart in the right ventricle RV and to deliver stimulation pulses to the right ventricle RV. A third lead 50 is here shown to be introduced into the right atrium RA and is able to sense or deliver signals in this right atrium RA with the help of the sensors or electrodes 51, 52. The leads 30, 40, 50 are formed by electrical conductors, or other conductors, in order to conduct signals between the sensor or electrode members 31, 32, 33, 41, 42, 51, 52 and the control circuit 14, as is known those skilled in the art.

The device 10 also may be provided with a drug delivery system 60, which makes it possible to deliver a drug into the body in which the device 10 is implanted. The device 10 also may be provided with a warning signal emitter 70 for generating a warning signal. The warning signal may be communicated, for example, via wireless communication to an external device in the possession of the person into whom the device 10 is implanted, or in the processor of a physician.

The control circuit 14 thus receives signals from the first sensor 33, and thus receives signals related to the blood constituent. The control circuit 14 also senses the electrical activity of the heart, via signals from one or more sensors or electrodes 31, 32, 33, 41, 42, 51, 52. Thereby, events signifying a heart cycle are detectable by the control circuit 14. The control circuit 14 also determines a first value related to the blood constituent during a first portion of the heart cycle and determines a second value related to the blood constituent during a second portion of the heart cycle. The different portions of the heart cycle may thus be detected by one or more of the sensors or electrodes.

A heart monitoring system according to the invention includes the heart monitoring device 10 together with one or more of the leads 30, 40, 50 and at least the first sensor 33 positioned on the lead 30.

FIGS. 2A-2E show the variation of different parameters for corresponding parts of a heart cycle. The X-axis represents time t and the Y-axis represents the different parameters. The systolic part of the heart cycle starts approximately at the hatched line 61 and ends at approximately the hatched line 62, where the diastolic portion of the heart cycle starts.

Figure 2:
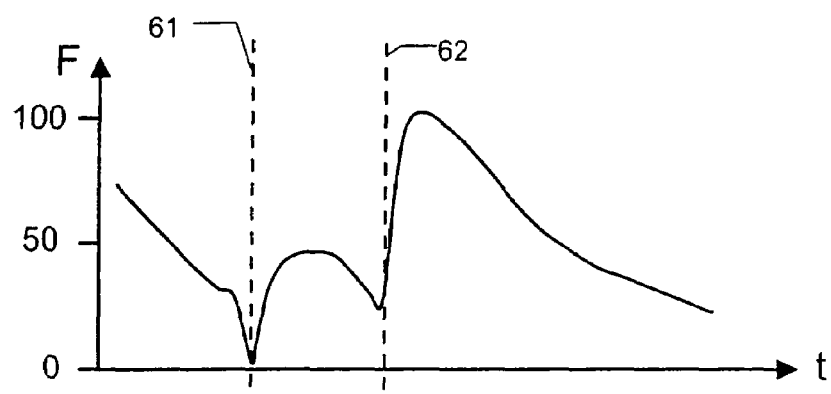
FIG. 2A shows schematically the coronary blood flow.
FIG. 2B shows schematically the aortic blood flow.
FIG. 2C shows schematically the blood flow in the coronary sinus.
FIG. 2D shows schematically the partial pressure of oxygen in the coronary sinus at rest.
FIG. 2E shows schematically an electrocardiogram.
Figure 2:
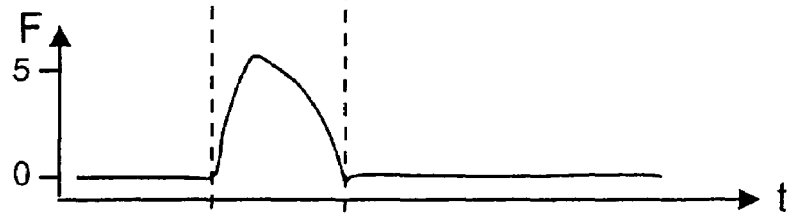
Figure 2:
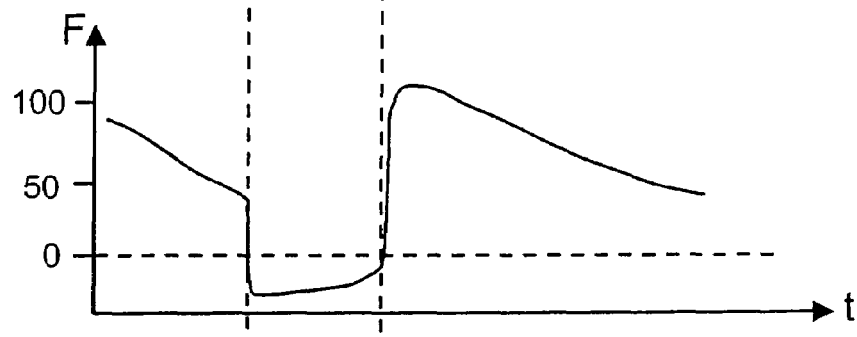
Figure 2:
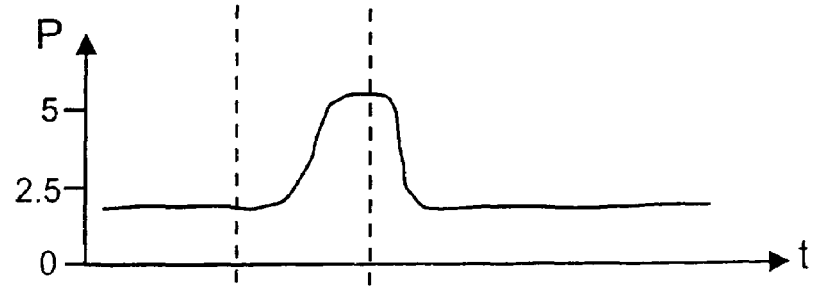
Figure 2:
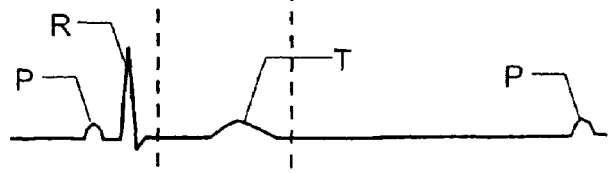

FIG. 2A shows schematically the blood flow in ml/mm in the coronary artery.

FIG. 2B shows schematically the aortic blood flow in l/mm.

FIG. 2C shows very schematically an example of the blood flow in the direction out from the coronary sinus in ml/mm. It can be seen that during a portion of the heart cycle, primarily during the systolic portion, the blood flow is negative. This means that blood during this portion flows in from the right atrium RA into the coronary sinus. This happens normally during the ventricular contraction.

FIG. 2D shows very schematically an example of how the partial pressure of oxygen, in kPa, may vary in the coronary sinus during the heart cycle. During the systolic phase, in particular during the latter 70% or the latter half of the systolic portion of the heart cycle, the oxygen partial pressure represents the oxygen partial pressure in mixed venous blood, since, as explained above, the mixed venous blood from the right atrium RA tends to enter into the coronary sinus. Before the start of the systolic portion of the heart cycle, the partial pressure of oxygen in the coronary sinus represents the partial pressure of oxygen in the coronary venous blood.

FIG. 2E shows an electrocardiogram (ECG) during the heart cycle shown in the figures. P here represents the P-wave, R represents the QRS-complex and T represents the T-wave.

The concentration of different constituents of blood carries information about the heart condition. For example, the concentration of nitric oxide indicates the vasoconstriction-vasodilatation and therefore, if measured in the cardiac venous blood, may be used as an indication of biochemical events. The amount of lactic acid, and thereby the pH-value, indicates whether anaerobic metabolism occurs. The different blood constituents may differ in cardiac venous blood as compared to in mixed venous blood. This fact is used according to the present invention in order to monitor the cardiac function and to detect if the heart does not function properly. In the description below, the partial pressure of oxygen will be used as an example of a blood constituent. It should be noted that the quantities mentioned are only given as examples. These quantities may vary between different living beings. The different quantities and the criteria for carrying out different measures therefore should be adapted to the particular living being using the invention.

When the living being is at rest, the partial pressure of oxygen in mixed venous blood may be about 5.3 kPa. The oxygen partial pressure in coronary venous blood in the coronary sinus may be about 2.3 kPa. When the living being in question is at a higher activity level (exercise), the oxygen partial pressure in mixed venous blood can decrease to about 2.0 kPa. The oxygen partial pressure in the cardiac venous blood normally does not decrease substantially during exercise but remains at approximately 2.3 kPa. At hard exercise, the partial pressure of oxygen in the cardiac venous blood may be reduced to about 2.0 kPa. These insights may be used to control a heart monitoring device according to the present invention.

Figure 3:
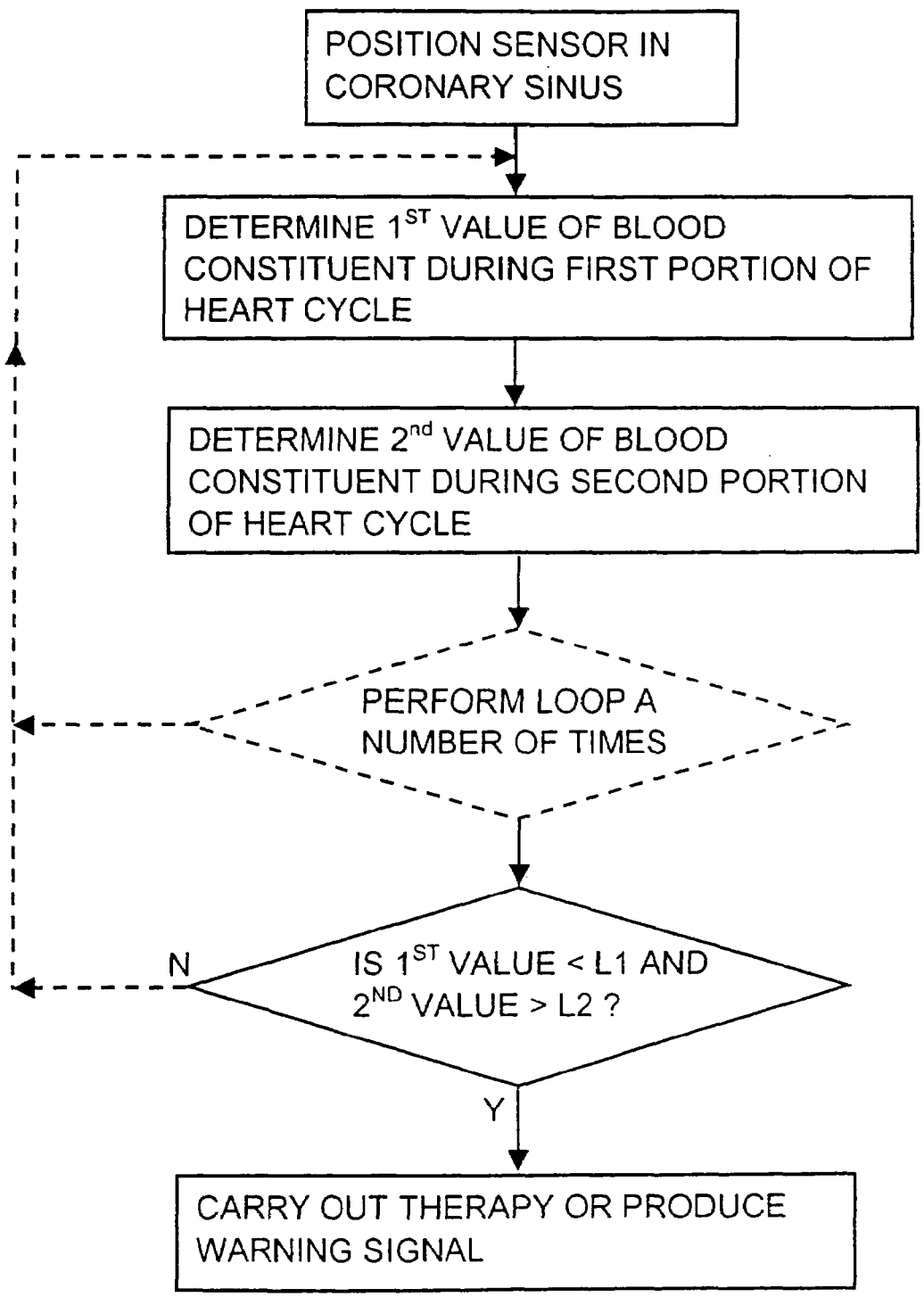
FIG. 3 shows a flowchart of the use of a heart monitoring system according to an embodiment of the invention.
Figure 4:
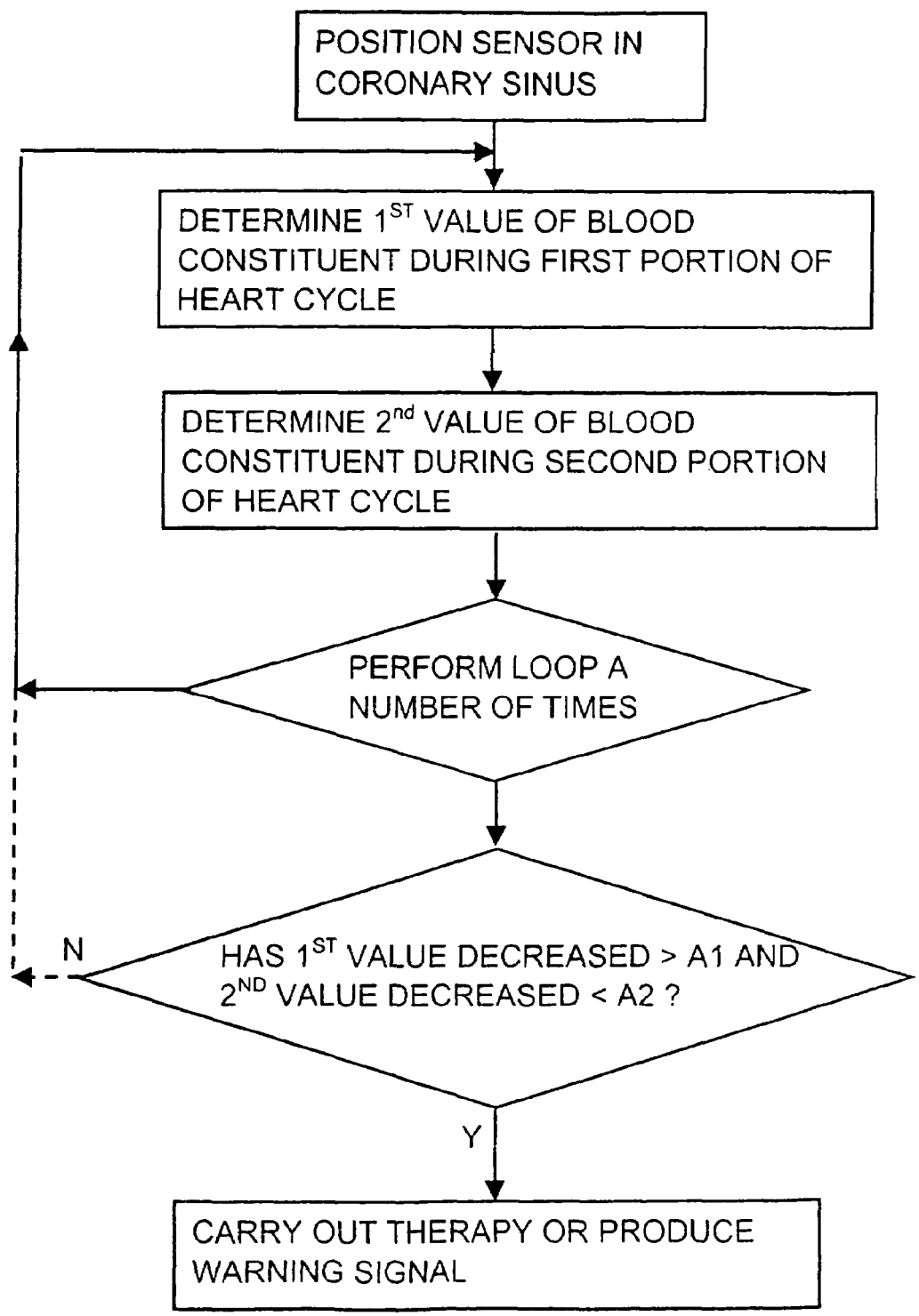
FIG. 4 shows a flowchart of the use of a heart monitoring system according to another embodiment of the invention.

FIGS. 3 and 4 are flowcharts for the use of a heart monitoring system according to different embodiments of the invention. At the same time, FIGS. 3 and 4 show how the heart-monitoring device according to the invention operates. FIG. 3 thus shows that a sensor, i.e. the aforementioned first sensor member 33, is positioned in the coronary sinus of a living being. How to insert a lead into the coronary sinus is well known to those skilled in the art and therefore need not be explained in more detail. The control circuit 14 determines a first value of the blood constituent during a first portion of the heart cycle. Furthermore, the control circuit 14 determines a second value related to the blood constituent during a second portion of the heart cycle. Of course, the first portion of the heart cycle is always different from the second portion of the heart cycle. The control circuit 14 can operate such that said first value of the blood constituent, in this example the partial pressure of oxygen, is measured during the diastolic portion of the heart cycle. The control circuit 14 may operate such that this first value is measured substantially around the P-wave. The control circuit also measures the second value of the blood constituent during the systolic portion of the heart cycle. Preferably, the second value is measured during the later 70% of the systolic portion of the heart cycle, for example substantially about the time of the occurrence of the T wave. The first value thus is related to the oxygen partial pressure in coronary venous blood and the second value is related to the partial pressure of oxygen in primarily mixed venous blood.

Preferably, the control circuit 14 monitors the first and second values over a number of heart cycles. In FIG. 3, this is represented by the loop that is performed a number of times. This can be done in order to achieve a reliable value, for example by determining said first and second values as an average value over some heart cycles. It is also possible to monitor the first and second values over several heart cycles, or all the time, in order to monitor how these values change with time.

The control circuit 14 triggers the heart-monitoring device to carry out at least one measure if the first and second values and/or a relationship between said first and second values fulfill a predefined condition. If the predefined condition is not fulfilled, then no particular measure is carried out, but the device may directly or later carry out a new determination of the first and second values. This is indicated by the hatched line starting at N. The predefined condition may be that the first value is tower than a first predefined level L1 and the second value is higher than a second predefined level L2. If, the first value, i.e. the partial pressure of oxygen in the cardiac venous blood, is lower than, for example, 2.1 kPa while the second value, i.e. the partial pressure of oxygen in mixed venous blood, is higher than, for example, 3.0 kPa, then a measure can be carried out. The described situation means that the partial pressure of oxygen in mixed venous blood indicates that the living being in question is not under hard exercise although the partial pressure of oxygen in cardiac venous blood is quite low. This is an indication that the heart does not function properly, for example due to overload or due to an ischemic event. The measure to be carried out may be, for example, to control the delivery of stimulation pulses to the heart, for example by reducing the pacing rate, or to deliver a drug or to deliver a warning signal as described above.

FIG. 4 shows another example of how the heart-monitoring device according to the invention may operate. The first steps are here the same as in connection with FIG. 3. The loop is performed a number of times. In this case, however, predefined condition is that the first value has decreased more than a first predefined amount A1 over a number of heart cycles while the second value has decreased less than the second predefined amount A2 over said plurality of heart cycles. The first predefined amount may be that the partial pressure of oxygen in the cardiac venous blood has fallen more than, for example, 0.2 kPa (or a certain percentage of the original value), while the partial pressure of oxygen in mixed venous blood has decreased less than, for example, 1.0 kPa (or a certain percentage of the original value). This, again, is an indication of the fact that the heart is not working properly. Also in this case, the measure can be that the delivery of stimulation pulses to the heart is controlled, that a drug is released or that a warning signal is delivered. It should be noted that it is of course possible to combine the two manners of operating the device disclosed in FIGS. 3 and 4.

FIGS. 3 and 4 thus also show manners of using the heart monitoring system according to the invention. The system may thus be used in order to detect a state of overload or ischemia in the heart. As mentioned above, the system may be arranged such that stimulating pulses may be delivered to both the ventricles RV, LV of the heart. The device 10 and the system may of course be arranged such that the delivery of the stimulation pulses is changed in an iterative process based on the detected and monitored first and second values. In this manner, the delivery of the stimulation pulses may be adjusted until a more normally operating heart condition is detected. As mentioned above, the control circuit 14 may also sense the physical activity level of the living being into which the device 10 is implanted. In this manner, a further indication of the activity level of the living being in question is obtained. The control circuit 14 may detect whether the first and second values, or the change of the first and second values, correspond to that which is considered normal when the living being in question is at rest or is at a high activity level.

Although the invention has primarily been described in connection with sensing the partial pressure of oxygen, the invention is also applicable to other blood constituents like those mentioned above. For example, the half-time of nitric oxide is very short. This means that mixed venous blood will contain small amounts of nitric oxide while the level in the coronary venous blood is highly dependent on the intrinsic regulation of the cardiac perfusion. Therefore, similar conditions to those described above may be predefined for controlling the heart monitoring device also in response to the detection of first and second values concerning nitric oxide. Different predefined conditions, of course, may be set up for the different blood constituents.

Examples of different sensors that may be used are given in the documents cited above. For example, a sensor suitable for detecting the partial pressure of oxygen is given in the above-cited U.S. Pat. No. 6,236,873.

Although modifications and changes may be suggested by those skilled in the art, it is the intention of the inventor to embody within the patent warranted hereon all changes and modifications as reasonably and properly come within the scope of his contribution to the art.

I claim:

1. An implantable heart monitoring device comprising:
   a control circuit;
   a first sensor adapted to be disposed in a coronary sinus region of a heart to sense blood oxygen in said coronary sinus region, and supplying a first sensor signal representing a blood oxygen level to the control circuit;
   at least one further sensor adapted to interact with the heart to sense activity of the heart, said at least one further sensor supplying a further sensor signal representing said activity to the control circuit; and
   said control circuit, from said further sensor signal, identifying a first portion in a diastolic portion, and a second portion in a systolic portion, of a same heart cycle of the heart, and from said first sensor signal, determining a first value related to said blood oxygen level that occurs during said first portion and identifying said first value as having occurred during said first portion and determining a second value related to said blood oxygen level that occurs during said second portion and identifying said second value as having occurred during said second portion, and said control circuit emitting an output signal indicative of functioning of the heart dependent on a relation between said first value and said second value.

2. An implantable heart-monitoring device as claimed in claim 1 wherein said control device detects said second value in said second portion within a final 70% of said diastolic portion.

3. An implantable heart-monitoring device as claimed in claim 1 wherein said control circuit detects said first and second values in each of a plurality of heart cycles of the heart.

4. An implantable heart monitoring device as claimed in claim 1 comprising a therapeutic device that executes an action related to cardiac therapy, wherein said control circuit emits a control signal to said therapeutic device that controls said action upon an occurrence selected from the group consisting of said first value fulfilling a predetermined condition, said second value fulfilling a predetermined condition, and a relationship between said first value and said second values fulfilling a predetermined condition.

5. An implantable heart monitoring device as claimed in claim 4 wherein said occurrence is said relationship between said first value and said second value fulfilling a predetermined condition, and wherein said predetermined condition is said first value being lower than a first predetermined level and said second value being higher than a second predetermined level.

6. An implantable heart monitoring device as claimed in claim 4 wherein said occurrence is said relationship between said first value and said second value fulfilling a predetermined condition, and wherein said predetermined condition is said first value decreasing by more than a first predetermined amount over a plurality of heart cycles while said second value decreases less than a second predetermined amount over said plurality of heart cycles.

7. An implantable heart monitoring device as claimed in claim 4 wherein said therapeutic device is a stimulation pulse generator which emits stimulation pulses to the heart, and wherein said action is delivery of said stimulation pulses to the heart.

8. An implantable heart monitoring device as claimed in claim 4 wherein said therapeutic device is a drug delivery device that delivers a drug to a subject in whom said heart monitoring device is implanted, and wherein said action delivery of said drug.

9. An implantable heart-monitoring device as claimed in claim 4 wherein said therapeutic device is a warning signal generator, and wherein said action is to emit a warning signal.

10. An implantable heart monitoring device as claimed in claim 4 further comprising an activity level sensor that senses a level of physical activity of a subject in whom the heart monitoring device is implanted, said activity sensor supplying an activity level signal to said control circuit, and said control circuit determining whether to emit said control signal dependent on said occurrence and said activity level.

11. An implantable heart monitoring system comprising:
a control circuit;
a lead arrangement connected to said control circuit and configured for implantation in a subject;
a first sensor carried by said lead arrangement and adapted to be disposed in a coronary sinus region of a heart to sense blood oxygen in said coronary sinus region, and supplying a first sensor signal representing a blood oxygen level to the control circuit;
at least one further sensor carried by said lead arrangement and adapted to interact with the heart to sense activity of the heart, said at least one further sensor supplying a further sensor signal representing said activity to the control circuit; and
said control circuit, from said further sensor signal, identifying a first portion in a diastolic portion, and a second portion in a systolic portion,
of a same heart cycle of the heart, and from said first sensor signal, determining a first value related to said blood oxygen level that occurs during said first portion and identifying said first value as having occurred during said first portion and determining a second value related to said blood oxygen level that occurs during said second portion and identifying said second value as having occurred during said second portion, and said control circuit emitting an output signal indicative of functioning of the heart dependent on a relation between said first value and said second value.

12. An implantable heart-monitoring system as claimed in claim 11 wherein said control device detects said second value in said second portion within a final 70% of said diastolic portion.

13. An implantable heart-monitoring system as claimed in claim 11 wherein said control circuit detects said first and second values in each of a plurality of heart cycles of the heart.

14. An implantable heart monitoring system as claimed in claim 11 comprising a therapeutic device that executes an action related to cardiac therapy, wherein said control circuit emits a control signal to said therapeutic device that controls said action upon an occurrence selected from the group consisting of said first value fulfilling a predetermined condition, said second value fulfilling a predetermined condition, and a relationship between said first value and said second values fulfilling a predetermined condition.

15. An implantable heart monitoring system as claimed in claim 14 wherein said occurrence is said relationship between said first value and said second value fulfilling a predetermined condition, and wherein said predetermined condition is said first value being lower than a first predetermined level and said second value being higher than a second predetermined level.

16. An implantable heart monitoring system as claimed in claim 14 wherein said occurrence is said relationship between said first value and said second value fulfilling a predetermined condition, and wherein said predetermined condition is said first value decreasing by more than a first predetermined amount over a plurality of heart cycles while said second value decreases less than a second predetermined amount over said plurality of heart cycles.

17. An implantable heart monitoring system as claimed in claim 14 wherein said therapeutic device is a stimulation pulse generator which emits stimulation pulses to the heart, and wherein said action is delivery of said stimulation pulses to the heart.

18. An implantable heart monitoring system as claimed in claim 14 wherein said therapeutic device is a drug delivery device that delivers a drug to a subject in whom said heart monitoring device is implanted, and wherein said action is delivery of said drug.

19. An implantable heart-monitoring system as claimed in claim 14 wherein said therapeutic device is a warning signal generator, and wherein said action is to emit a warning signal.

20. An implantable heart monitoring system as claimed in claim 14 further comprising an activity level sensor that senses a level of physical activity of a subject in whom the heart monitoring device is implanted, said activity sensor supplying an activity level signal to said control circuit, and said control circuit determining whether to emit said control signal dependent on said occurrence and said activity level.

21. An implantable hear monitoring system as claimed in claim 11 wherein said lead arrangement includes a first lead carrying said first sensor, and wherein said implantable heart monitoring system further comprises an electrode also carried on said first lead, said first lead having a distal end and said electrode being carried on said first lead closer to said distal end than said first sensor, and wherein said first lead is configured to introduce said electrode via the coronary sinus into a cardiac vein.

22. An implantable heart monitoring system as claimed in claim 21 wherein said control circuit includes circuitry that generates stimulation pulses, and wherein said stimulation pulses are delivered via said first lead and said electrode.

23. An implantable hear monitoring system as claimed in claim 21 wherein said lead arrangement includes a second lead carrying a further electrode adapted for positioning in the right ventricle of the heart.

24. A heart monitoring method comprising the steps of:
disposing a first sensor in a coronary sinus region of a heart and sensing at least blood oxygen in said coronary sinus region with said first sensor, and generating a first sensor signal representing blood oxygen level;
disposing at least one further sensor adapted to interact with the heart and sensing activity of the heart with said at least one further sensor, and generating a further sensor signal representing said activity; and
from said further sensor signal, electronically identifying a first portion in a diastolic portion, and a second portion in a systolic portion of a same heart cycle of the heart, and from said first sensor signal, electronically determining a first value related to said blood oxygen level that occurs during said first portion and identifying said first value as having occurred during said first portion and a second value related to said blood oxygen level that occurs during said second portion and identifying said second value as having occurred during said second portion, and emitting an output signal indicative of functioning of the heart dependent on a relation between said first value and said second value.

25. A heart monitoring method as claimed in claim 24 comprising electronically detecting said second value in said second portion within a final 70% of said diastolic portion.

26. A heart monitoring method as claimed in claim 24 comprising electronically detecting said first and second values in each of a plurality of heart cycles of the heart.

27. A heart monitoring method as claimed in claim 24 comprising executing a therapeutic action related to cardiac therapy, upon an occurrence selected from the group consisting of said first value fulfilling a predetermined condition, said second value fulfilling a predetermined condition, and a relationship between said first value and said second values fulfilling a predetermined condition.

28. A heart monitoring method as claimed in claim 27 wherein said occurrence is said relationship between said first value and said second value fulfilling a predetermined condition, and wherein said predetermined condition is said first value being lower than a first predetermined level and said second value being higher than a second predetermined level.

29. A heart monitoring method as claimed in claim 27 wherein said occurrence is said relationship between said first value and said second value fulfilling a predetermined condition, and wherein said predetermined condition is said first value decreasing by more than a first predetermined amount over a plurality of heart cycles while said second value decreases less than a second predetermined amount over said plurality of heart cycles.

30. A heart monitoring method as claimed in claim 27 comprising emitting stimulation pulse to the heart, and controlling delivery of said stimulation pulses to the heart as said therapeutic action.

31. A heart monitoring method as claimed in claim 27 comprising delivering a drug to the subject in whom said heart monitoring device is implanted, and controlling delivery of said drug as said therapeutic action.

32. A heart monitoring method as claimed in claim 27 comprising emitting a warning signal as said therapeutic measure.

33. A heart monitoring method as claimed in claim 27 comprising sensing a level of physical activity of the subject in whom the heart monitoring device is implanted, and generating an activity level signal, and electronically determining whether to execute said action dependent on said occurrence and said activity level.

* * * * *